United States Patent
Kessler et al.

(10) Patent No.: US 7,141,286 B1
(45) Date of Patent: Nov. 28, 2006

(54) TAMPER EVIDENT SYRINGE ASSEMBLY

(75) Inventors: Patricia Marie Kessler, Newbury Park, CA (US); John Ackermann, Thousand Oaks, CA (US)

(73) Assignee: Amgen, Inc., Thousands Oaks, CA (US)

(*) Notice: Subject to any disclaimer, the term of this patent is extended or adjusted under 35 U.S.C. 154(b) by 0 days.

(21) Appl. No.: 09/958,723

(22) PCT Filed: Apr. 13, 2000

(86) PCT No.: PCT/EP00/03345

§ 371 (c)(1),
(2), (4) Date: Dec. 26, 2001

(87) PCT Pub. No.: WO00/62848

PCT Pub. Date: Oct. 26, 2000

(30) Foreign Application Priority Data

Apr. 14, 1999 (EP) .................................. 99107291

(51) Int. Cl.
*B65D 41/32* (2006.01)
*B65D 39/00* (2006.01)
*B65D 83/04* (2006.01)
*G07F 11/68* (2006.01)
*A61M 5/00* (2006.01)

(52) U.S. Cl. .................... 428/41.8; 428/213; 215/230; 221/170; 206/534; 604/256; 604/111

(58) Field of Classification Search .............. 428/40, 428/41.8, 343, 213, 215, 214, 212; 206/807; 215/246, 230, 232; 604/256, 111, 182, 189, 604/218, 131; 221/70; 383/5; 40/300

See application file for complete search history.

(56) References Cited

U.S. PATENT DOCUMENTS

| 3,074,542 A | * | 1/1963 | Myerson et al. ............ 206/365 |
| 3,667,657 A | | 6/1972 | Chiquiar-Arias |
| 3,777,949 A | | 12/1973 | Chiquiari-Arias |
| 5,232,455 A | * | 8/1993 | Hollister ..................... 604/192 |
| 5,257,704 A | * | 11/1993 | Gutt .......................... 215/246 |
| 5,506,015 A | * | 4/1996 | Frederiksen et al. ....... 428/41.8 |

(Continued)

FOREIGN PATENT DOCUMENTS

DE 19 66 623 B2 8/1973

(Continued)

OTHER PUBLICATIONS

Official communication (along with translation) received from Japanese Patent Office dated Mar. 8, 2004.

*Primary Examiner*—Nicholas D. Lucchesi
*Assistant Examiner*—Roz Maiorino
(74) *Attorney, Agent, or Firm*—Marshall, Gerstein & Borun LLP

(57) ABSTRACT

The present invention relates to pre-filled tamper evident syringe assemblies, including a tubular syringe body with a nose portion for receiving a hollow needle communicating with the interior of the syringe body, a needle cap for protecting at least the nose portion and a label bonded to an outer surface of the syringe body. The tamper evident feature of such an assembly is provided by a simple construction. Therefore, at least a portion of the needle cap adjacent to the syringe body is of essentially the same diameter as the syringe body, and the label of the syringe body extends onto the needle cap and is bonded and/or positively engaged thereto, so as to produce evidence of tampering when the needle cap is removed.

24 Claims, 3 Drawing Sheets

U.S. PATENT DOCUMENTS

| | | | |
|---|---|---|---|
| 5,651,775 A | 7/1997 | Walker et al. | 604/207 |
| 5,823,997 A | 10/1998 | Thorne | 604/110 |
| 6,190,364 B1 * | 2/2001 | Imbert | 604/256 |
| 6,305,541 B1 * | 10/2001 | Tanner et al. | 206/366 |
| 2001/0003150 A1 * | 6/2001 | Imbert | |

FOREIGN PATENT DOCUMENTS

| | | |
|---|---|---|
| DE | 31 40 398 A1 | 9/1982 |
| DE | 44 12 754 A1 | 10/1995 |
| DE | 43 14 090 C2 | 9/1997 |
| DE | 42 36 393 A1 | 6/1998 |
| EP | 0 071 290 A1 | 2/1983 |
| JP | 07-289639 | 11/1995 |
| JP | 7289639 | 11/1995 |
| JP | 3024311 | 5/1996 |
| JP | 10-254361 | 9/1998 |
| JP | 10254361 | 9/1998 |
| JP | 10-305478 | 11/1998 |
| JP | 10-305823 | 11/1998 |
| JP | 10305478 | 11/1998 |
| JP | 10305823 | 11/1998 |

* cited by examiner

TAMPER EVIDENT SYRINGE ASSEMBLY

This invention relates to a tamper evident syringe assembly, including a tubular syringe body with a nose portion for receiving a hollow needle communicating with an interior of the syringe body, a needle cap for protecting at least the nose portion and a label bonded to an outer surface of the syringe body. The invention also relates to a pre-filled tamper evident syringe assembly and a tamper evident label for use in a syringe assembly.

Pre-filled syringes are widely known, especially in fields where liquid medicaments are used and where such injectables may be administered by the patients themselves. Pre-filled syringes minimize packaging by eliminating the need for a separate vial of medication. They are also even more convenient than disposable syringes which require filling before use. Due to the fact that a single dose product is provided, which is already accurately filled and labeled with the name of the medication, no incorrect dosage upon administration can occur. There is as well a lower risk of contamination of the medicament with micro-organisms, including potentially deadly viruses. Pre-filled syringes also minimize the space required for storage and shipment.

PRIOR ART

Known syringe assemblies, especially pre-filled ones, include a barrel or tubular syringe body containing an injectable solution. The majority of such assemblies include a nose portion provided at one end of the syringe body on which a hollow needle is fitted. The hollow needle can be either separate from the barrel or integrated thereon as a unit. The rear side of the syringe body is closed by a plunger assembly including a plunger head for sealing the barrel in one direction and a shaft extending out of the barrel. To fit a separate hypodermic needle to the nose portion, well known fittings, such as a luer lock design can be used. Since it is important that the injectable be safely housed within the barrel, the nose portion with or without the needle, also has to be safely sealed. This is done by a needle cap fitting thereon. Modern cap designs include an outer rigid shield and an elastic, hollow core for inserting the nose portion with or without the needle. The elastic core provides for proper sealing. One further important aspect of syringes, especially pre-filled ones, is to make them tamper evident and to limit access. Known syringe assemblies are therefore stored in blister packages which completely surround the assembly and which must be opened to gain access. The blister package therefore provides for evidence of tampering. One disadvantage of such a design is the relatively large amount of packaging material, especially in cases where several of these assemblies are sold as a bigger supply unit. Each of the assemblies in the supply unit has to be packed in the blister package separately. Some medications may have to be cold-stored, which means that the blister package material must be appropriate for cold storage to ensure that the seal does not break in cold temperatures.

Evidence of tampering is necessary also in the food industry and several solutions have been provided. However, none of the solutions can be directly transferred to syringe assemblies, especially due to the small size of the syringes, preferably pre-filled ones, and other obstacles in the pharmaceutical field.

It is an object of the present invention to provide a syringe assembly which is provided with a simple tamper evident feature, which is easily manufactured at a low cost.

A further object of the present invention is to reduce the amount of waste occurring from the tamper evident feature.

SUMMARY OF THE INVENTION

According to the present invention, the above objects are obtained with a tamper evident syringe assembly according to the preamble of claim 1, with the features that at least a portion of the needle cap adjacent to the syringe body is of essentially the same diameter as the syringe body and that the label of the syringe body extends onto the needle cap and bonded and/or positively engaged thereto, so as to produce evidence of tampering when the needle cap is removed. It is not necessary that the assembly is pre-filled. The tamper evident feature is therefore fulfilled by simply extending the label onto the needle cap. The portion of the label extending onto the needle cap has to be securely connected thereto by either a bonding technique or by positively engaging it. This portion of the label can be either designed so that it has to be destroyed when separating the needle cap from the syringe body, or that it prevents proper re-assembly of the cap. The term diameter should not be limited to only cylindrical shapes of the syringe body and the needle cap. Other shapes can be used and the term diameter represents the dimensions of the outer shapes. According to a similar solution in claim 14 a pre-filled tamper evident syringe assembly is provided.

In one preferred embodiment, the label is wrapped around the syringe body and/or the needle cap at least, in an angle range of about at least three-hundred and sixty degrees. Since the label is wrapped totally around the syringe body or the needle cap, it is not easy to separate these parts. Especially in cases where the syringe body and/or the needle cap, is manufactured from material with insufficient bonding characteristics, such as a glass material, it is useful that the label has overlapping parts which can be bonded together more securely. An overlapping part of the label on the needle cap provides for proper connection over the full range.

In another form, an inner surface of the label can be provided with a layer of permanent adhesive. For example, in cases where the needle cap is removed from the front portion of the label, leaving a hollow tube formed by this part, it is impossible to stick the needle cap back onto the nose portion due to the fact that the permanent adhesive is still active and provides for a high friction force. This part of the label will crease if someone tries to put the needle cap back onto the nose portion.

In another embodiment, a crease line is formed in the label between the label portion extending onto the needle cap and the remainder of the label. Such a crease line can be perforated, for example in the area between the needle cap and the syringe body, so that the label portion extending onto the needle cap is separated from the remainder of the label if the needle cap is removed. It is also possible to have additional indications, such as different colors in the area of the perforation.

According to one further aspect of the invention, an acrylic adhesive can be used as the permanent adhesive. Such an adhesive provides for high bonding strength even at low temperatures.

Although any other suitable plastic material can be used for providing a film to create the label, according to one preferred embodiment, a PVC film (polyvinylchloride) is used. Such a film has good flexibility even at low temperatures and especially in cases where a perforation is provided, and undesired breaking of the perforation is to be avoided.

A still more common material for medical purposes is polypropylenbe (PP) and it is therefore also possible to make the label from a PP film.

In one further arrangement, the label portion extending onto the needle cap can be provided with a pull-tab. The needle cap can therefore be only removed from the syringe body, if the front label portion is pulled away from the remainder of the label by using the pull-tab.

One further advantage is provided by an embodiment wherein the label portion extending onto the needle cap is provided with at least one opening and the needle cap is provided with at least one projection extending through at least one opening.

The needle cap therefore positively engages the label portion and it has to be destroyed to remove the needle cap. Any kind of openings and projections can be designed to fulfill this feature.

To ensure a proper connection of the needle cap portion and the label portion, it is also possible to provide the needle cap portion on which the label is bonded with a rough surface. This can be done either to increase the bonding characteristics in connection with an adhesive or to provide a surface shape, for example by knurling, around which the label portion is wrapped tightly. In this regard it is also possible to use a shrinkable film to tightly engage at least the needle cap portion.

In one further aspect of the present invention, the label portion bonded onto the needle cap can be formed from an elongated strip connected through bridging portions to the remainder of the label, the bridging portions at least laterally confined with at least one opening. The strip can be made longer than the remainder of the label so that for example, a pull tab can be provided. It is also possible that such a design is simply cut out from a film in one piece.

Preferably, the label portion bonded onto the needle cap can have two rectangular openings. The openings abut the crease line and the elongated strip and the bridging portions laterally confine the openings. This will reduce the force necessary to separate the label portion from the remainder of the label, since it is not connected along the whole crease line with the rest of the label. Using such a design, the force for separating the label portion can be exactly defined.

The invention is also directed to a tamper evident label for use in a syringe assembly according to one of claims 1 to 26. The label has a portion, which is bondable to an outer surface of a syringe body and a portion, which is bondable and/or positively engageable to a portion of a needle cap having essentially the same diameter as the syringe body.

DESCRIPTION OF PREFERRED EMBODIMENTS OF THE INVENTION

Figure 2:
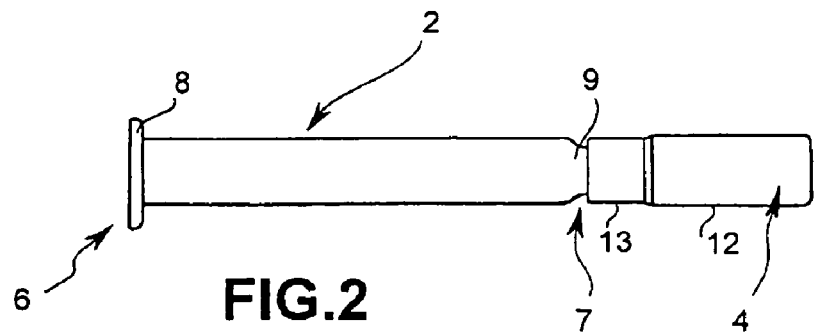
FIG. 2 is a plan view of the tubular syringe body and the needle cap assembled thereto.

FIGS. 1 to 4 show a first embodiment of the present invention.

In these figures a pre-filled tamper evident syringe assembly (1), essentially including a tubular syringe body (2), a plunger assembly (3) slideably fitted therein, a needle cap (4) and a tamper evident label (5) bonded to the syringe body and the needle cap is shown.

The syringe body (2) preferably is made out of a glass material and has opposing ends 6 and 7 and incorporates a chamber, preferably a cylindrical chamber, which is defined by the inner wall of the syringe body (2). End (6) is provided with a surrounding flange (8) and is open so that the plunger assembly (3) can be slideably received by the chamber. The end (7) is provided with a nose portion which is adapted to receive a hypodermic needle thereon. For example, a luer lock assembly can be used to connect the hypodermic to the nose portion (9). The hypodermic needle having a channel extending from the tip of the needle into the chamber of the syringe body (2). This channel of the needle preferably is sealed with an appropriate design of needle cap (4).

The plunger assembly extending through the end (6) includes a shaft (10) which has a thumb rest (11) located at the outer end of the shaft (10). At the inner end of the shaft (10) a moveable plug is provided which is in sliding engagement with the inner wall of the chamber of the syringe body (2). The thumb rest (11) is adapted to facilitate the application of pressure on the shaft (10) to move the plunger assembly (3) along the chamber within the syringe body (2).

The chamber within the syringe body (2) is filled with the desired injection fluid. Any leakage is prevented by the sliding plug of the plunger assembly (3) and the needle cap (4).

The needle cap (4) comprises an outer needle shield manufactured from rigid material and an inner core made from an elastic rubber material which can be the same material as used for the sliding plug of the plunger assembly (3). This resilient material of the needle cap (4) seals the channel of the needle or the nose portion (9). The needle cap (4) has an enlarged gripping portion (12) and a reduced diameter portion (13). The reduced diameter portion (13) is generally of the same diameter as the syringe body (2) at the nose portion to which it attaches. The gripping portion (12) is only slightly bigger in diameter, preferably adding twice the thickness of the tamper evident label (5). If label (5) is bonded to the syringe body (2) and the needle cap (4), the labeled syringe body (2) and gripping portion (12) have the same diameter.

Figure 1:
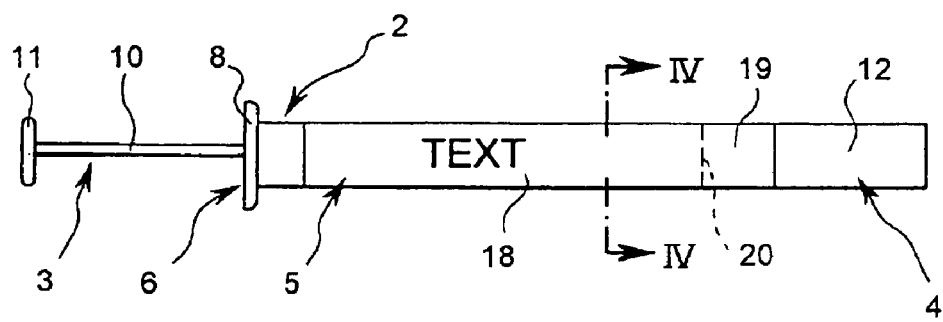
FIG. 1 is a plan view of a pre-filled tamper evident syringe assembly.
Figure 4:
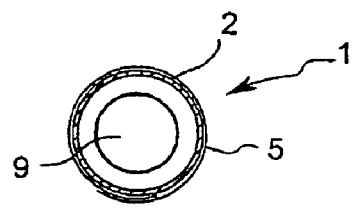
FIG. 4 is an enlarged view of a cross-section of the syringe assembly of FIG. 1 along the line IV—IV of FIG. 1.

As can be seen in FIG. 1, the plunger assembly (3) is in the extended position when the syringe assembly (1) is filled.

The tamper evident label (5) is manufactured from a thin film of polypropylene cut to rectangular shape and having two shorter edges 14 and 15, and two longer edges 16 and 17. The width of the label (5) or the length of the shorter edges 14 and 15 is longer than the circumference of the syringe body (2), so that the edge portions 16 and 17 must overlap if the label (5) is bonded to the syringe body (2) (See FIG. 4). The front side of the tamper evident label (5) may be provided with printing which gives information of the substance filling the syringe assembly (1). The rear side of the tamper evident label (5) is covered with a permanent adhesive, preferably an acrylic adhesive.

Figure 3:
FIG. 3 is a plan view of a tamper evident label before bonding to the syringe body and the needle cap.

This can be seen in FIGS. 1 and 3, the tamper evident label (5) is divided into two portions. On the left side there is the body portion (18) which is bonded to the syringe body (2) and which may show written information of the syringe contents, and on the right side there is a cap portion (19) which is bonded to the reduced diameter portion (13) of the needle cap (4). The body portion (18) and the cap portion (19) are separated from each other by a crease line or perforation (20), which extends substantially parallel to the shorter edges (14) and (15) of the label (5). As can also be seen, the cap portion (19) is smaller than the body portion (18). The distance between the short edge (15) and the crease line or perforation (20) is such that the crease line or perforation (20) is positioned near the end face of the cap (4) or at the area where the nose portion (9) extends into the syringe body (2). The cap portion (19) is bonded by the permanent adhesive to the needle cap (4) and the body portion (18) is bonded to the outer surface of the syringe body (2).

The crease line or perforation (20) is of significant strength, so that the needle cap (4) can only be removed from the syringe body (2) by providing a predetermined force. Preferably the needle cap (4) is rotated about the axis of the syringe assembly (1) and the label (5) twists and breaks at the perforation (20). Sufficient evidence of tampering is provided due to the destruction of the label (5) at the perforation (20). Once the needle cap (4) is removed, the plunger assembly (3) can be engaged by pushing on the thumb rest (11).

Syringe assemblies (1) may be sold in cardboard boxes, six or eight assemblies (1) per box. Each of the syringe assemblies (1) is positioned in the cardboard box by clamping devices which hold the syringe assembly (1) in place. Due to the tamper evident label (5) each of these syringe assemblies (1) is provided with a proper indication of tamper. The material used to manufacture the label (5) and used for the adhesive is such that even cold storage of these assemblies (1), if necessary, is not a problem.

It can be understood from the above that the pre-filled tamper evident syringe assembly (1) of the present invention does not produce as much package material waste as has been the case with blister packaging of the prior art syringe packaging.

Figure 5:
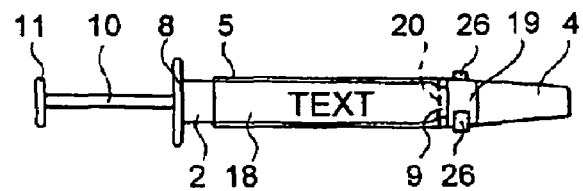
FIG. 5 is a plan view of a second embodiment of a pre-filled tamper evident syringe assembly with a transparent label.
Figure 6:
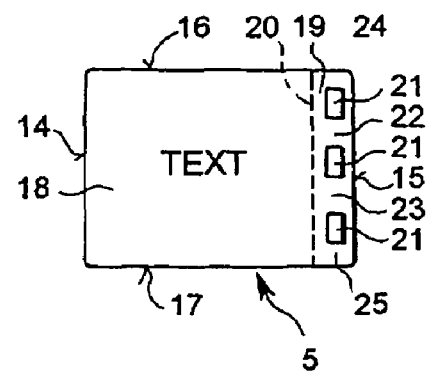
FIG. 6 is a plan view of the tamper evident label of FIG. 5 prior to bonding.

A further embodiment of the assembly (1) is shown in FIGS. 5 and 6. Identical or similar elements use the same reference designations as are used with regard to these elements referenced above. Only the main distinctions are described in the following.

The major distinction of the embodiment of FIGS. 5 and 6 as seen therein, is that the cap portion (19) of the label (5) is provided with openings (21), preferably rectangular openings, which are of identical size. Three of such openings (21) are provided in line and exactly in the middle between the short edge (15) and perforation line (20). The three openings (21) are separated from each other through bridging portions (22) and (23), as well as spaced apart from longer edge (16) by bridging portion (24) and spaced apart from edge (17) by bridging portion (25).

The needle cap (4) is provided with at least one projection (26), which extends through the openings (21) of the label (5). This means, that the projection(s) (26) positively engage the openings (21), when the label is bonded to the syringe body (2). With such an embodiment, it is not necessary to provide the rear side of the cap portion (19) of the label (5) with an adhesive, although this could be done. The body portion (18) of the label (5) is provided with an adhesive as usual and bonded to the syringe body (2).

If the needle cap (4) is separated from the syringe body (2) the projection(s) (26) pull the cap portion (19) the label away from the body portion (18) of the label along the perforation or crease line (20).

Figure 7:
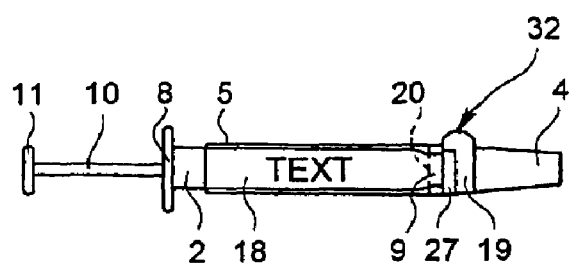
FIG. 7 is a plan view of a third embodiment of a pre-filled tamper evident syringe assembly with a transparent label.
Figure 8:
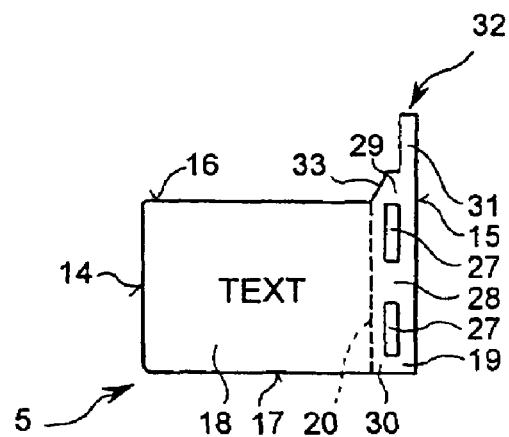
FIG. 8 is a plan view of the label of FIG. 7 prior to bonding.

A third embodiment is now described with respect to FIGS. 7 and 8. Only the distinctions relative to the above embodiments are described in detail. Therefore, identical reference signs indicate identical or similar elements as referenced above.

The label (5) of this embodiment only includes two openings (27), preferably rectangular openings, separated from each other by a bridging portion (28). The outer ends of the openings (27) are confined by bridging portions (29) and (30).

The cap portion (19) is formed from an elongated strip (31) connected to the body portion (18) by the bridging portions (28, 29 and 30). The openings (27) thereon immediately abut the perforation (20) so that the cap portion (19) is only connected at three areas with the body portion (18). The upper part of the elongated strip (31) forms a pull tab (32) when the label (5) is bonded to the syringe body (2) and the needle cap (4).

The size of the openings (27) has a direct influence on the force needed to separate the cap portion (19) from the body portion (18). The force required to separate the portions, therefore, can be controlled. Although in the embodiment of FIGS. 7 and 8 the cap portion (19) may be bonded by an adhesive to the needle cap (4), projections at the needle cap (4) which extend through the openings (27) as in the foregoing embodiment can be used.

As can be seen from FIG. 8, whereas the edge (17) extends longitudinally, the upper edge (16) is stepped near and within the capped portion (19) to either provide for the pull tab (32) and an inclined edge portion (33) for proper separation along the perforation or crease line (20).

Figure 9:
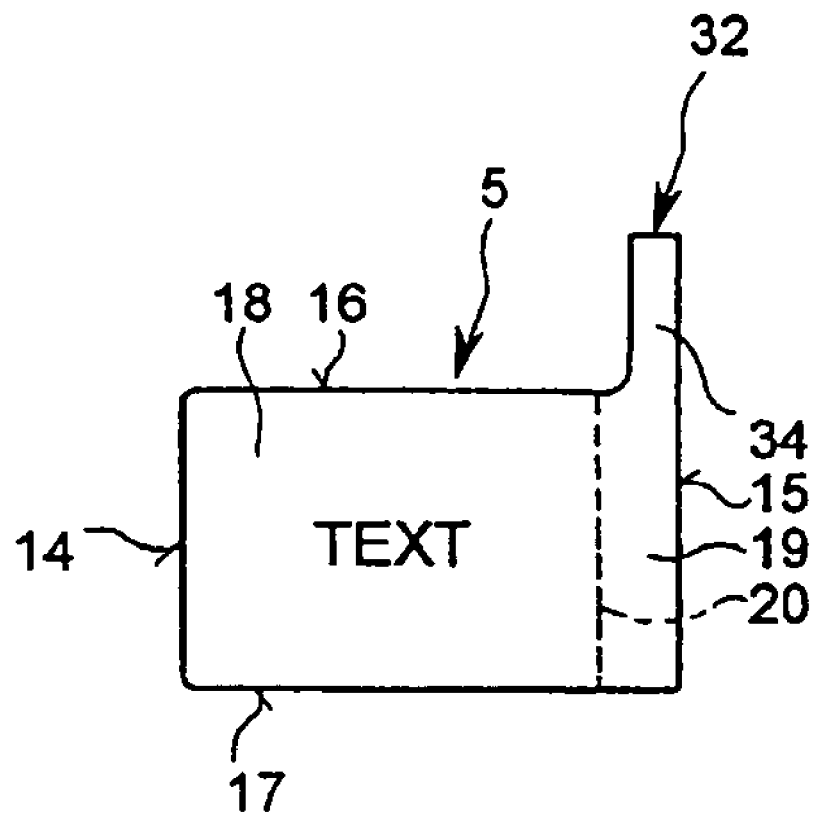
FIG. 9 is a plan view of another tamper evident label prior to bonding.

In FIG. 9 a further embodiment of a tamper evident label (5) is shown which is distinguished from the label of FIG. 3 by an elongated strip (34) to provide a pull tab (32).

The respective embodiments shown in the present invention are only examples for illustration and do not restrict the present invention. One skilled in the art will appreciate that other modifications may be envisioned, all of which are intended to be encompassed within the scope of the following claims. Especially, all features described herein can be combined with one another.

What is claimed is:

1. A syringe assembly comprising:
   a tubular syringe body with a nose portion adapted to receive a hollow needle and communicating with an interior of the syringe body,
   a cap adjacent to the syringe body adapted to protect at least the nose portion, at least a portion of the cap proximate to the syringe body being substantially a same diameter as the syringe body, and
   a tamper evident label bonded to an outer surface of the syringe body and at least the proximate cap portion, the label having a syringe body portion and a cap portion, wherein the cap portion of the label is provided with at least one opening and the proximate cap portion is provided with at least one projection extending through the at least one opening.

2. An assembly according to claim 1, wherein the label is wrapped around at least one of the syringe body and the proximate cap portion at an angle of at least 360 degrees.

3. An assembly according to claim 1, wherein an inner surface of at least a portion of the label is provided with a layer of permanent adhesive.

4. An assembly according to claim 3, wherein the permanent adhesive comprises an acrylic adhesive.

5. An assembly according to claim 1, wherein a crease line is formed in the label between the syringe body portion of the label and the cap portion of the label.

6. An assembly according to claim 5, wherein the cap portion of the label is provided with a pull tab.

7. An assembly according to claim 1, wherein the label is made from a PVC film.

8. An assembly according to claim 1, wherein the label is made from a PP film.

9. An assembly according to claim 1, wherein the proximate cap portion to which the label is coupled has a rough surface.

10. An assembly according to claim 9, wherein the proximate cap portion is knurled and the cap portion of the label is wrapped securely around the proximate cap portion.

11. An assembly according to claim 10, wherein the cap portion of the label is formed from an elongated strip connected through bridging portions to the syringe body portion of the label, the bridging portions laterally defining the at least one opening in the cap portion of the label.

12. An assembly according to claim 11, wherein the cap portion of the label has two openings, the openings abut a crease line formed between the syringe body portion of the label and the cap portion of the label, and the elongated strip and bridging portions laterally defining the openings.

13. A pre-filled syringe assembly comprising:
a tubular syringe body with a nose portion adapted to receive a hollow needle and communicating with an interior of the syringe body,
a cap adjacent to the syringe body adapted to protect at least the nose portion, at least a portion of the cap proximate to the syringe body being substantially a same diameter as the syringe body, and
a tamper evident label bonded to an outer surface of the syringe body and at least the proximate cap portion, the label having a syringe body portion and a cap portion, wherein the cap portion of the label is provided with at least one opening and the proximate cap portion is provided with at least one projection extending through the at least one opening.

14. An assembly according to claim 13, wherein the label is wrapped around at least one of the syringe body and the proximate cap portion at an angle of at least 360 degrees.

15. An assembly according to claim 13, wherein an inner surface of at least a portion of the label is provided with a layer of permanent adhesive.

16. An assembly according to claim 15, wherein the permanent adhesive comprises an acrylic adhesive.

17. An assembly according to claim 13, wherein a crease line is formed in the label between the syringe body portion of the label and the cap portion of the label.

18. An assembly according to claim 17, wherein the cap portion of the label is provided with a pull tab.

19. An assembly according to claim 13, wherein the label is made from a PVC film.

20. An assembly according to claim 13, wherein the label is made from a PP film.

21. An assembly according to claim 13, wherein the proximate cap portion to which the label is coupled has a rough surface.

22. An assembly according to claim 21, wherein the proximate cap portion is knurled and the cap portion of the label is wrapped securely around the proximate cap portion.

23. An assembly according to claim 22, wherein the cap portion of the label is formed from an elongated strip connected through bridging portions to the syringe body portion of the label, the bridging portions laterally defining the at least one opening in the cap portion of the label.

24. An assembly according to claim 23, wherein the cap portion of the label has two openings, the openings abut a crease line formed between the syringe body portion of the label and the cap portion of the label, and the elongated strip and bridging portions laterally defining the openings.

* * * * *